United States Patent
Mavliev

(10) Patent No.: US 6,710,874 B2
(45) Date of Patent: Mar. 23, 2004

(54) METHOD AND APPARATUS FOR DETECTING INDIVIDUAL PARTICLES IN A FLOWABLE SAMPLE

(76) Inventor: Rashid Mavliev, 357 W. Rincon Ave., Unit C, Campbell, CA (US) 95008

( * ) Notice: Subject to any disclaimer, the term of this patent is extended or adjusted under 35 U.S.C. 154(b) by 0 days.

(21) Appl. No.: 10/188,981

(22) Filed: Jul. 5, 2002

(65) Prior Publication Data

US 2004/0004716 A1 Jan. 8, 2004

(51) Int. Cl.⁷ ................... G01N 15/02; G01N 33/36
(52) U.S. Cl. .................... 356/336; 356/246
(58) Field of Search .................... 356/336, 337, 356/338, 436, 440, 246

(56) References Cited

U.S. PATENT DOCUMENTS

| | | | |
|---|---|---|---|
| 3,873,203 A | | 3/1975 | Friedman et al. |
| 4,983,038 A | | 1/1991 | Ohki et al. |
| 5,007,732 A | | 4/1991 | Ohki et al. |
| 5,125,737 A | * | 6/1992 | Rodriguez et al. ............ 356/39 |
| 5,159,403 A | | 10/1992 | Kosaka |
| 5,311,290 A | * | 5/1994 | Olson et al. ................. 356/634 |
| 5,414,508 A | * | 5/1995 | Takahashi et al. .......... 356/246 |
| 5,521,699 A | | 5/1996 | Kosaka et al. |
| 5,548,395 A | | 8/1996 | Kosaka |
| 5,650,847 A | | 7/1997 | Maltsev et al. |
| 5,663,503 A | | 9/1997 | Dam et al. |
| 5,690,895 A | | 11/1997 | Matsumoto et al. |
| 5,710,069 A | | 1/1998 | Farkas et al. |
| 5,721,433 A | | 2/1998 | Kosaka et al. |
| 5,739,902 A | | 4/1998 | Gjelsnes et al. |
| 5,818,583 A | | 10/1998 | Sevick-Muraca et al. |
| 5,824,269 A | | 10/1998 | Kosaka et al. |
| 5,835,211 A | | 11/1998 | Wells et al. |
| 5,880,835 A | | 3/1999 | Yamazaki et al. |
| 5,948,684 A | | 9/1999 | Weigl et al. |
| 5,972,710 A | | 10/1999 | Weigl et al. |
| 6,109,119 A | | 8/2000 | Jiang et al. |
| 6,136,272 A | | 10/2000 | Weigl et al. |
| 6,159,739 A | | 12/2000 | Weigl et al. |
| 6,211,956 B1 | | 4/2001 | Nicoli |

* cited by examiner

Primary Examiner—Frank G. Font
Assistant Examiner—Layla Lauchman
(74) Attorney, Agent, or Firm—Burns, Doane, Swecker & Mathis, LLP

(57) ABSTRACT

An apparatus and method are disclosed for the optical characterization of particles in highly concentrated systems (i.e. suspensions and dispersions, hereinafter referred to as the "sample"), such as solid-particle slurries and liquid-in-liquid (e.g. oil-in-water) emulsions, which do not require dilution of the samples. Reduction of the optical transparency of the sample, which is required to avoid the influence of multiple light scattering, is achieved by forming the sample into a sheet flow with controlled thickness. The sample transparency is measured by using a light extinction method and the sample thickness in the optical cell is controlled in order to keep the sample transparency within a range of predetermined values. By this means, an improved efficiency of single-particle detection is achieved and the usual reduction of signal quality due to multiple light scattering is avoided.

36 Claims, 9 Drawing Sheets

METHOD AND APPARATUS FOR DETECTING INDIVIDUAL PARTICLES IN A FLOWABLE SAMPLE

BACKGROUND OF THE INVENTION

1. Field of the Invention

The invention relates generally to the field of detection and characterization of particles in concentrated liquid systems, such as slurries and suspensions.

2. Background Information

Liquid systems with high particulate concentrations are widely used in industry. Examples of such systems are slurries used in Chemical Mechanical Planarization (CMP) processes for the semiconductor industry and emulsions used in the pharmaceutical industry.

Slurry systems used for CMP can have a complicated chemical and colloidal composition. Regarding the chemical composition, a slurry can be either basic (relatively high pH) or acidic (relatively low pH). Keeping the pH value in a predetermined range is often desired for slurries because the pH value often determines the stability of the colloidal composition of the slurry. The colloidal composition of the slurry can have a wide distribution of particle sizes, with diameters ranging from, for example, tens of nanometers (nm) to tens of micrometers (um). The concentration of particles may vary from, for example, $~10^{12}$ particles per cubic centimeter (#/cc) for submicron particles to ~1–100 #/cc for larger (>1 $\mu$m) particles. The size distribution of particles in slurries typically can not be described by a single function but rather, often includes several independent modes. Monitoring particle size parameters is often desired for CMP applications because the size distribution of the small particles can determine the CMP performance. For example, large particles with diameters larger than a few micrometers can cause wafer damage.

Optical methods of detection and characterization have been used for non-intrusive, on-line monitoring of particle parameters in gas and liquid media. See, for example, U.S. Pat. No. 6,159,739, the disclosure of which is hereby incorporated by reference in its entirety. Optical methods include irradiation of the sample with light of known parameters (e.g. wavelength and intensity) and analysis of the scattered and/or transmitted light using different optical detectors.

Integral optical methods, also known as "ensemble" optical methods, allow in principle for the determination of the particle parameters of the scattering system as a whole. With these methods, particles of different sizes and compositions contribute simultaneously to the detected "signal". Deconvolution of this composite "signal", using an appropriate mathematical algorithm, is used to arrive at an estimate of the underlying particle size distribution. These integral optical methods usually involve several assumptions, such as the type (e.g., shape) of the size distribution, refractive index, and so forth.

Differential optical methods allow for the determination of the parameters of single particles. Accumulation of the information relating to the plurality of individual particles allows for the determination of the parameters of the system at whole. Because of the statistical nature of this process, the sensing volume is an important parameter for differential optical methods. The sensing volume is defined as that part of the sample suspension or dispersion, which is irradiated and from which the optical signal is collected. The larger the sensing volume, the greater the number of particles can typically be detected per given sampling period. At the same time, a larger sensing volume can generate larger scattering noise, which can ultimately determine the limit for particle detection. The optimal sensing volume can be determined by taking into account the degree of sample transparency, the concentration of smaller particles, the concentration of bigger particles, and so forth.

Application of optical methods for particle characterization of slurries and suspensions is often limited because of the high optical density of the sample, caused primarily by the high concentration of smaller particles. The high optical density of slurries and suspensions can cause multiple light scattering and a large blockage of light propagation through the sample. At these conditions it can be hard to obtain reliable and accurate information about the size distribution of the particles that scatter and/or block light.

The frequently wide variation in particle parameters of a liquid system can also create conflicting requirements. The sensing volume should be large enough to provide a statistically representative signal for the largest particles, having the lowest number concentration. However, the larger sensing volume can cause a higher optical density (turbidity) of the sample and more extensive multiple light scattering. In addition, a high concentration of abrasives in a slurry can damage optical cell surfaces that are in contact with the sample flow.

It would be desired to have the largest possible sensing volume, consistent with limitations imposed by the optical density and multiple light scattering of the sample. In addition, it would be desired to employ a differential method of optical detection to retain high resolution and sensitivity to the small number of relatively large particles that populate the particle size distribution and which largely define the quality of the slurry. Integral, or "ensemble", methods of optical detection are significantly limited in their resolution and sensitivity in this respect.

U.S. Pat. No. 5,710,069 (Farkas et al.) discloses a method for measuring slurry particle size during substrate polishing, the disclosure of which is hereby incorporated by reference in its entirety. This method includes shining a light into a portion of the moving liquid-particle mixture having small numbers of relatively large particles and detecting and measuring the reflected light to determine the sizes of the particles. The signal includes a background due to scattered light from a relatively large, indeterminate number of particles. This scattered light is caused in part by the plurality of smaller particles that are present in a slurry at high concentrations.

Another known optical method which does not require slurry dilution, is described by Cerni and Sehler (Particle Optical Sensing for CMP Slurry, MICRO, 2000), and based on measuring the intensity of transmitted and scattered light of different wavelengths. This method involves data processing to reconstruct the underlying particle size distribution. It is an indirect method, which does not allow for the detection of single particles of larger size existing on a background of smaller particles at much higher concentration.

Another optical detection method is described in U.S. Pat. No. 5,818,583 by Sevick-Muraca et al. A system and method are disclosed for the self-calibrating, on-line determination of size distribution and volume fraction of a number of particles dispersed in a medium by detecting multiple scattered light from the particles. The multiple scattered light is re-emitted in response to exposure to a light source configured to provide light of time varying intensity at selected wavelengths. An estimation approach based on an expected shape of the size distribution and the mass of the particles is also disclosed.

U.S. Pat. No. 5,835,211 (Wells et al.) discloses an optical sensor for counting and sizing particles, the disclosure of which is hereby incorporated by reference in its entirety. This method includes measuring a light extinction (LE) and a light scattering (LS) signal representative of the particles. The light scattering and light extinction signals are combined to form a single composite signal, which increases in magnitude monotonically with an increase in the size of the particle passing through a beam of light. The combination of LS and LE signals allows an accurate measurement of particle size in both an upper range and lower range of particle sizes. The slurry is diluted for this monitoring technique to work properly, because only one particle should pass through the beam of light at a time. Additionally, a small sample of the slurry is first extracted and then substantially diluted before being analyzed. The analysis is therefore accomplished off-line, and therefore a delay can exist between the extraction of the slurry sample and the subsequent determination of the particle size distribution parameters.

A television system can be used to analyze an optical signal scattered by particles (Mavliev, R., 1992 Optical Determination of Size and Concentration of Particles below 100 nm: Method and Applications, In: *Nucleation and Atmospheric Aerosols*. Eds.: Fukuta, Wagner, A. Deepak Publishing, Hampton, VI, USA, 377–380). This approach divides the total sensing volume into approximately $10^3$–$10^4$ smaller sub-volumes. The optical signal from each sub-volume is registered independently, resulting in a signal/noise ratio increase of approximately 1000 times. Detecting a signal from sub-volumes independently allows extending the range of measurable particulate concentrations. That is, the probability of coincidence of single particles can be reduced and the detectable concentration can be increased. This approach can be a partial solution for detection of signals from small particles of high concentration systems but is not known to be applied directly for slurries and emulsions with smaller concentrations.

Dilution of slurry samples, which is used by most optical methods, is not a desirable process because it can alter the particle size distribution parameters of the slurry, depending on the method and amount of dilution. It also can change the initial size distribution of the particles in a slurry (see Cerni and Sehler) because of the process of agglomeration or by introduction of foreign (contamination) particles associated with the fluid-used to dilute the initial concentrated slurry. Additionally, the concentration of the largest particles decreases substantially during extensive dilution, causing a reduction in statistics and therefore increased time to accumulate reliable particle size distribution information. Errors in the computed dilution coefficient directly affect the accuracy of the particle size distribution measurement relating to the original, concentrated sample.

In summary, dilution of the concentrated starting slurry sample is undesirable because particle size-parameters can, and often do, change; additional particles are usually introduced during the dilution process; and the concentration of the largest particles decreases significantly as a result of substantial dilution of the staring slurry sample.

Hydrodynamic focusing of a flowing fluid containing particles is used in scanning flow cytometry (Maltsev, 2000, Scanning flow cytometry for individual particle analysis, *Review of Scientific Instruments*, 71:243–255, the disclosure of which is hereby incorporated by reference in its entirety). Hydrodynamic focusing is based on delivering two concentric flows of fluid through a confined channel, or capillary. The outer "sheath" flow is usually comprised of clean water (or other fluid), while the inner flow carries the particles to be measured. The inner flow diameter can be as small as 10 microns $\mu$m. Using liquid flow cytometry, biological particles in suspension can be counted and classified in a rapid and reliable manner. The sample fluid containing the particles of interest is introduced into the focusing cell along with a transport liquid. The particles pass substantially one at a time through the flow cell, where they pass through an intense focused beam of light. The result is that the particles can be counted individually and analyzed, or measured, with regard to their "signatures" of light scattering and fluorescence intensities. At present, liquid flow cytometry is employed for the analysis of white blood cells (leukocytes), and in the field of bacteriology. Examples can be found in U.S. Pat. Nos. 6,136,272 by Weigl et al.; in 6,109,119 by Jiang et al.; in 5,880,835 by Yamazaki et al.; and in 5,824,269 by Kosaka et al, the disclosures of which are hereby incorporated by reference in their entirety. Liquid flow cytometry methods have not been applied to concentrated slurry systems, because known methods do not take into account the typical high optical density of slurry systems caused by the existence of high concentrations of smaller particles.

Other documents of interest are as follows: U.S. Pat. No. 6,211,956 (Nicoli); 6,159,739 (Weigl et al.); 6,136,272 (Weigl et al.); 6,109,119 (Jiang et al.); 5,972,710 (Weigl et al.); 5,948,684 (Weigl et al.); 5,880,835 (Yamazaki et al.); 5,835,211 (Wells); 5,824,269 (Kosaka et al.); 5,818,583 (Sevic-Muraca et al.); 5,721,433 (Kosaka); 5,710,069 (Farkas et al.); 5,650,847 (Maltsey et al.); 5,690,895 (Matsumoto et al.) 5,663,503 (Kosaka); 5,548,395 (Kosaka); 5,159,403 (Kosaka); 5,007,732 (Ohki et al.); 4,983,038 (Ohki et al.); 5,739,902 (Gjelsnes et al.); 5,521,699 (Kosaka et al.) and 3,873,204 (Friedman et al.), the disclosures of which are hereby incorporated by reference in their entireties.

Similarly, the disclosures of the following documents are hereby incorporated by reference: Cerni and Sehler. Particle Optical Sensing for CMP Slurry, MICRO, 2000; J Adorjan, et al., Particle sizing in strongly turbid suspensions with the one-beam cross-correlation dynamic light-scattering technique. Applied Optics, 1999, 38:3409–3416; N. L. Swanson, B. D. Billard, and T. L. Gennaro, Limits of optical transmission measurements with application to particle sizing techniques. Applied Optics, 1999, 38:5887–5893; H. Schnablegger and O. Glatter, Sizing of colloidal particles with light scattering: correction for beginning multiple scattering. Applied Optics, 1995, 34:3489–3501; and P. Nefedov et al., Application of a forward-angle-scattering transmissometer for simultaneous measurements of particle size and number density in an optically dense medium. Applied Optics, 1998, 37:1682–1689.

SUMMARY OF THE INVENTION

Exemplary embodiments of the present invention are directed to a non-intrusive method for in-line or off-line monitoring of single particles over a wide range of sizes and concentrations, contained in systems comprised mostly of smaller particles. Exemplary methods can accommodate mixtures without requiring their dilution, and mixtures wherein the "tail" of largest particles in the particle size distribution can be accurately measured. Optical characterization of particles over a wide range of sizes and concentrations in concentrated systems is achieved using exemplary embodiments wherein the sample flow is made relatively transparent. The transparency of the sample flow can be arranged in the form of a "sheet" flow, which is relatively thin in one dimension and wider in an orthogonal dimension. An exemplary optimal sample thickness can be determined using, for example, two criteria. The first criterion is based either on the absence of significant multiple scattering of light by the sample or the existence of relatively high sample transparency. The second criterion is based on the sensing volume necessary to obtain reliable statistical information on the large particles having a relatively low number concentration. For example, a sample fluid flow having a thickness in the range of approximately 5–500 μm and width of 5–20 mm can be established.

Generally speaking, exemplary embodiments relate to a method, and associated apparatus, for detecting individual particles in a flowable sample, comprising the steps of: hydrodynamically focusing the sample, the sample being opaque to at least a first range of wavelengths of lightwaves; measuring transarency of the sample; compressing the sample to create a compressed sample which is transparent to at least one of the wavelengths of lightwaves; and identifying characteristics of individual particles contained in the compressed sample.

A sample fluid flow can be placed into operable communication (e.g., at least partially surrounded) with a flow of clean (i.e. relatively particle-free) transparent liquid (e.g., water) or other appropriate liquid. An optical cuvette containing a hydrodynamically focused flow of the sample fluid can be used to form a sheet flow of the sample fluid. The cuvette includes a converging part, a flat part and a sample introduction part. In the flat part of the cuvette the width of the flow channel is narrow in one dimension. For example, 0.1 mm ±10% or lesser or greater) and wide in the orthogonal dimension (for example, approximately 10 mm±10% or lesser or greater). The flow channel parameters can be substantially constant (e.g., ±10% flow channel width in any direction) along the whole length of this flat part of the cuvette. The flat part of the cuvette is optically transparent and is used for characterization of the sample transparency and for the optical characterization of particles in the focused sample fluid.

BRIEF DESCRIPTION OF THE DRAWINGS

Other objects and advantages of the present invention will become apparent to those skilled in the art upon reading the following detailed description of preferred embodiments, in conjunction with the accompanying drawings, wherein like reference numerals have been used to designate like elements, and wherein.

DETAILED DESCRIPTION OF PREFERRED EMBODIMENTS

Figure 5A:
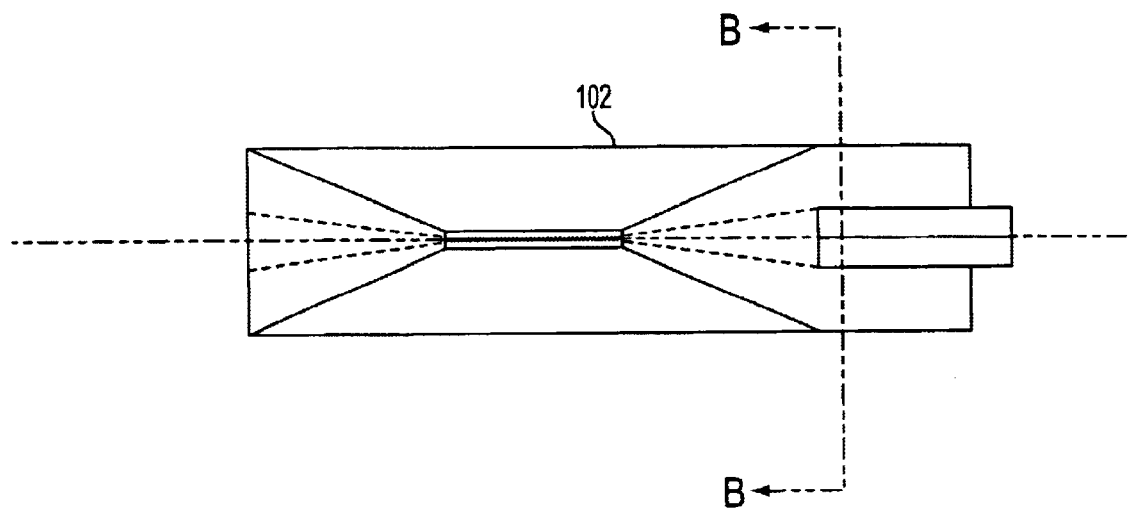
FIGS. 5A and 5B show an optical cuvette according to a fourth exemplary embodiment of the present invention.
Figure 5B:
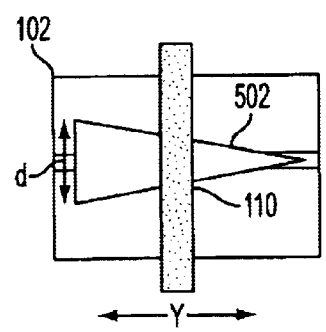

FIGS. 5A and 5B show an exemplary apparatus for detecting individual particles in a flowable sample, the apparatus being represented as a slurry monitoring system 100. The slurry monitoring system 100 includes means for hydrodynamically focusing the sample. The FIG. 1 hydrodynamically focusing means includes a slit for supplying the sample, and an additional slit for receiving a clean liquid, represented in the FIG. 1 embodiment as slurry and sheath flow inlets 101, 102 to an optical cuvette 102. An inlet to the cuvette 102 can assist in focusing the sample. In an exemplary embodiment, a ratio of the additional slit to the slit for supplying the sample can be at least 10:1, or can be any desired ratio selected as a function of the particular slurry characteristics and the characteristics of the particular clean liquid used. In an exemplary embodiment, the clean liquid (e.g., water) is any liquid having sufficient transparency to detect characteristics of the sample, and can have a pH matched to that of the sample. As referenced herein, the pH of the clean liquid and the sample are matched when they are approximately equal (±10%) or when they are of such relative pH that desired characteristics of the sample can still be monitored to a desired accuracy.

Because the sample is opaque to at least a first range of wavelengths of lightwaves, a means for compressing the sample can be used to create a compressed sample. A compressing means is represented in the exemplary FIG. 1 embodiment as windows (e.g., prisms) 104 and 106 having a gap formed within or between the windows, to compress the sample and render the sample transparent to at least one wavelength of lightwaves. The sample can be compressed to, for example, elongate the sample in a first dimension and/or a second dimension which is different from the first dimension. Those skilled in the art will appreciate that in any or all of the foregoing embodiments, as well as variations thereof, the cuvette can be configured using two optical windows, such as two Dove prisms to produce a flow cell for compressing the sample in at least one dimension to render the sample transparent to lightwaves of a predetermined wavelength.

Figure 1A:
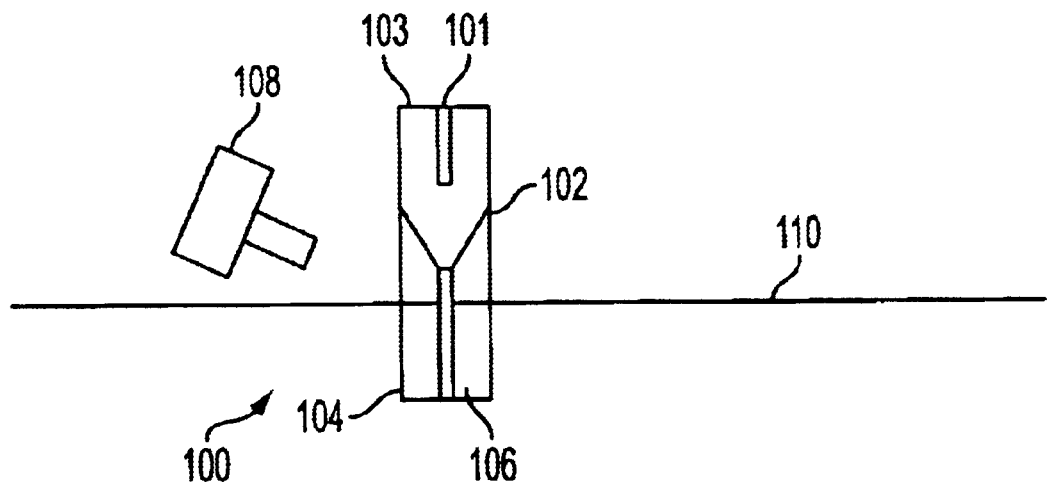
FIGS. 1A and 1B show a schematic diagram of a slurry monitoring system according to an exemplary embodiment of the invention.
Figure 1B:
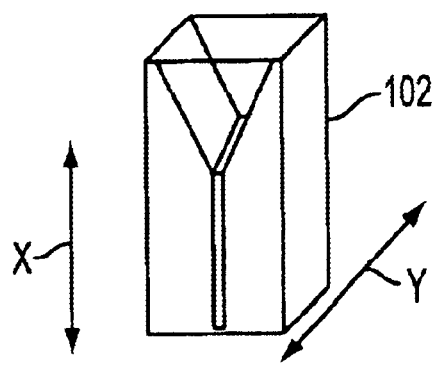

Means are provided for identifying characteristics of individual particles contained in the compressed sample. For example, the identifying means is represented in FIG. 1 as an optical detector 108 (e,g, a CCD camera, photodiode or other optically sensitive device) and an associated laser beam 110.

The compressing means contained within the optical cuvette 102 is represented as an optically transparent cell through which a clean liquid (e.g., flow of water or other liquid of sufficient transparency) is delivered, together with a flow of concentrated sample fluid ("slurry"). The slurry flow is formed into a thin layer with a typical thickness of 10–500 microns, located between two sheath flows of clean water or other transparent liquid. The sensing volume is formed by the intersection of this thin layer of slurry and an appropriately-shaped (typically a line source of approximately uniform intensity) beam of light from a laser or other suitable source.

The sample flow can be introduced into the converging part of the focusing cuvette at a predetermined distance from the flat part of the cuvette. In the converging part of the cuvette, the width of the flow channel changes smoothly from the point of entrance of the cuvette to the point at which the flat part of the cuvette commences. The sample introduction distance, width and shape of the sample introduction slit can vary as desired. These parameters can be used to determine the thickness of the sample fluid flow in the flat part of the cuvette and can be used to control the sample transparency and the optical sensing volume. The sample transparency can be measured by light extinction, and the sample fluid thickness in the flat part of the cuvette can be adjusted to obtain a predetermined transparency value or sensing volume value. Conventional light scattering and/or light extinction techniques can be used to measure the parameters of single particles having diameters above the detection limit. A CCD (charge-coupled device) detector/camera, together with appropriate frame-capture electronics and data-handling software, can be used to suppress the influence of background scattering on the quantitative detection of the signal produced by individual particles passing through the optical sensing volume.

Figure 2A:
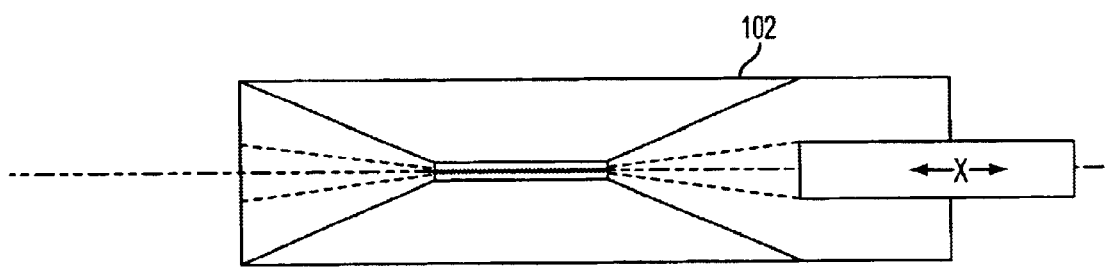
FIGS. 2A and 2B show an optical cuvette according to the first embodiment, wherein an X position of the slit determines a compression ratio and a thickness of the focused sample fluid in the flat part of the cuvette.
Figure 2B:
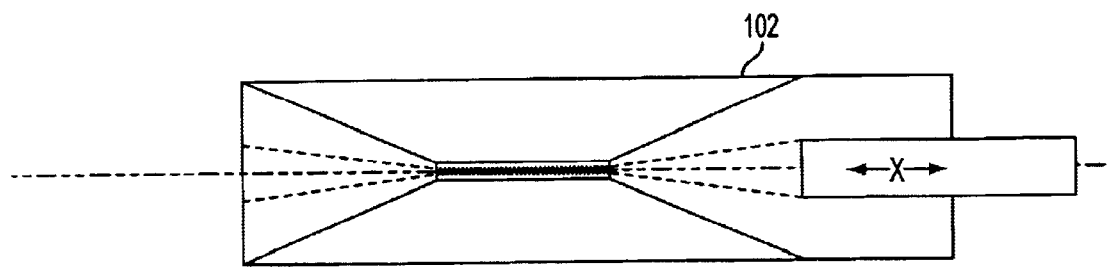

In an exemplary embodiment of the present invention, the sample flow is introduced into a converging inlet 112 of the cuvette at a predetermined distance from the entrance to the flat part 114 of the cuvette. This distance can be changed by translating a sample outlet 116 from the slurry inlet 101 along the X-axis of FIGS. 2A and 2B. The flow rate of the sample can be kept constant, usually in the range of 0.01–10 ml/sec., or can be varied as desired. The flow rate of the clean sheath fluid can be calculated using the width (along the narrow dimension) of the sample outlet flow, the width of the converging channel (along the narrow dimension) at the sample outlet location and the sample fluid flow rate. The focused sample fluid width in the flat part of the cuvette can be determined by the ratio of the width of the sample outlet flow and the width of the converging channel at the sample outlet location. This ratio can be multiplied by the thickness of the flow channel in the flat part of the cuvette to obtain the thickness of the focused sample fluid. Translation of the position of the sample outlet along the X-axis in the converging part of the cuvette, can be used to change the focused sample flow width in the flat part of the cuvette.

As shown in FIG. 1, the sample fluid flowing in the flat part of the cuvette is illuminated with a beam of light from a laser or any other suitable light source. The intensities of transmitted and/or scattered light are measured and analyzed to determine the sample fluid transparency (i.e. optical turbidity). One exemplary criterion of sample transparency can be the substantial absence of multiple light scattering. In the case of a lack of substantial sample transparency or the presence of excessive multiple light scattering, the width of the sample fluid flow can be adjusted by changing the position of the sample flow outlet in the converging channel. When the desired level of sample transparency is achieved, and/or the extent of multiple light scattering has been reduced to an acceptable, low level, the parameters of the particles in the sample fluid (e.g. the particle size distribution) can be measured optically with relatively high accuracy.

According to the Adorjan document, the Swanson et al document, the Schnablegger document and the Nefedov et al document, multiple light scattering is negligible for sample optical thicknesses below one (i.e. transmission>exp(−1)). The range of acceptable sample optical thickness can be extended up to five or more at small signal collection angles. In that case the correction of the Beer-Lambert light scattering law can be modified as described in the Nefedov et al document.

A means for filtering and recirculating the clean liquid can also be provided. For example, in the FIG. 1 embodiment, a pump, filter and recirculation conduit as will be discussed with respect to FIG. 8 can be provided for returning the clean liquid to a state of sufficient transparency that it can be used in a continuous process.

An exemplary method for using the FIG. 1 apparatus to detect; individual particles in a flowable sample includes steps of hydrodynamically focusing the sample, the sample being opaque to at least a first range of wavelengths of lightwaves; measuring of transparency of the sample; compressing the sample to create a compressed sample which is transparent to at least one of the wavelengths of lightwaves; and identifying characteristics of individual particles contained in the compressed sample. Sample transparency can be measured using, for example, the optical detector to sense the transmission and/or reflection of an emitted optical signal of known wavelength and intensity. That is, the intensity of a known signal transmitted through, and/or reflected by, the sample can be used to assess transparency.

Figure 3A:
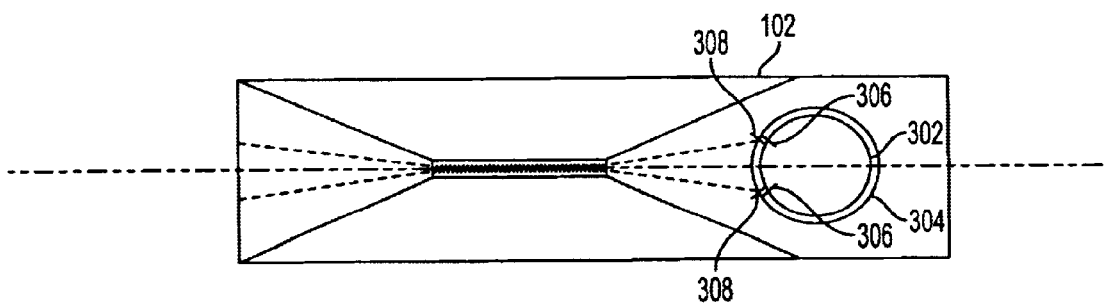
FIGS. 3A and 3B show an optical cuvette according to a second exemplary embodiment of the present invention.
Figure 3B:
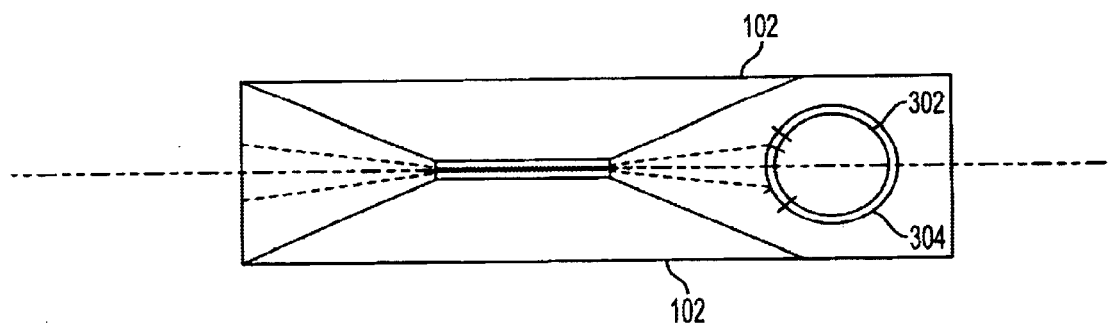

In another embodiment of the present invention as shown in FIGS. 3A and 3B, the sample fluid flow can be introduced into the converging part 112 of the focusing cuvette at a predetermined fixed distance from the flat part 114 of the cuvette. The width of the slit used to introduce the concentrated-sample fluid can be changed gradually by rotation of two coaxial tubes 302, 304 with fluid openings. The sample width is maximal when the edges 306, 308 of the openings in both tubes coincide. The choice of the extent of mismatch of the two openings allows the thickness of the focused sample fluid to be controlled.

The flow rate of the concentrated sample fluid can be kept constant typically in the range of 0.01–10 ml/sec., or can be varied as desired. The flow rate of the clean fluid sheath flow can be calculated to match the linear velocity of the sample fluid flow, using the width of the sample fluid outlet, the width of the converging channel at the sample outlet location and the sample flow rate, or any desired criteria. The focused sample fluid width in the flat part of the cuvette can be determined by the ratio of the (narrow) width of the sample fluid outlet nozzle and the (narrow) width of the converging channel at the sample outlet location. This ratio is multiplied by the thickness (in the thin dimension) of the flow channel in the flat part of the cuvette. Changing the sample fluid outlet width in the converging part of the cuvette changes the focused sample fluid width in the flat part of the cuvette. The sample fluid outlet width can be changed by, for example, compressing the sample fluid nozzle, or rotating the co-axial injection tubes.

The sample fluid in the flat part of the cuvette is illuminated with a light beam of appropriate shape from a laser or any other suitable light source. The intensities of transmitted and/or scattered light are measured and analyzed to determine the sample transparency. The width of the focused sample fluid flow can be adjusted so as to reach the desired level of sample transparency. When the desired level of sample transparency is achieved, the size parameters of the particles (for example, the particle size distribution above a given threshold diameter) in the sample fluid can be measured by known optical and electronic methods with relatively high accuracy. Changing the width of the sample fluid introduction slit causes a change in the sample fluid velocity at the slit outlet. The clean fluid sheath flow rate can be changed accordingly to avoid a mismatch in the velocities of the two fluids, which can result in turbulence mixing of the sample and sheath fluids.

Figure 4A:
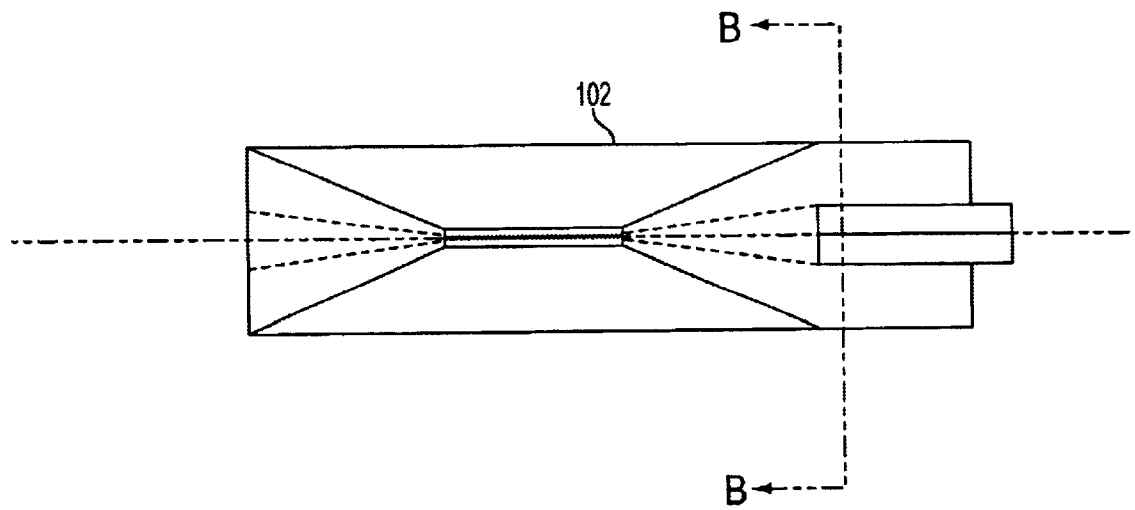
FIGS. 4A and 4B show an optical cuvette according to a third exemplary embodiment of the present invention.
Figure 4B:
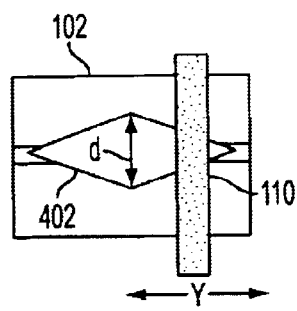

In the third and fourth embodiments of the present invention as shown in FIGS. 4A and 4B, and in FIGS. 5A and 5B, the sample fluid flow is introduced into the converging part of the focusing cuvette through a diamond shaped nozzle 402 (FIG. 4) or triangle shaped nozzle (FIG. 5), respectively. In FIGS. 4A and 4B, the width of the slit used to introduce the concentrated sample fluid is diamond-shaped, changing gradually from the center to each edge. The position of the incident light beam can be changed along the Y-axis, thereby allowing one to choose the desired sample fluid thickness for analysis.

In FIGS. 5A and 5B, a triangle shaped nozzle 502 is used wherein the width of the slit used to introduce the concentrated sample fluid is triangle-shaped, changing smoothly from one edge to the other. The position of the irradiating light beam can be changed along the Y-axis to select the desired sample thickness. The injection of the sample fluid occurs at a predetermined fixed distance from the start of the flat part of the cuvette.

The FIG. 4 diamond-shaped nozzle 402 has a maximum width at the center of the flow cross section, and the nozzle width gradually decreases along the axis Y. The FIG. 5 triangle shaped nozzle has a maximum thickness at one edge and zero thickness at the other edge of the flow cross section. The focused sample fluid width in the flat part of the cuvette can be determined from the ratio of the (narrow) width of the sample fluid outlet and the (narrow) width of the converging channel at the sample outlet location. This ratio can be multiplied by the thickness of the flow channel (along the thin dimension) in the flat part of the cuvette. In exemplary embodiments, the sample fluid thickness in the flat part of the cuvette will vary from substantially zero at the edges of the flow to a predetermined thickness at the center (or opposite edge) of the flow.

The sample fluid flow in the flat part of the cuvette can be illuminated with a light of appropriate shape from a laser or any other suitable light source. The intensities of transmitted and/or scattered light are measured along the Y-axis and analyzed to determine the sample transparency. Because the focused sample fluid width varies along the Y-axis, the sample transparency will vary accordingly. In the case of an absence of significant sample transparency, and/or the presence of excessive levels of multiple light scattering, the measuring position along the Y-axis can be adjusted. When the desired level of sample transparency is achieved, the size parameters of the particles (e.g. the particle size distribution above a given threshold diameter) in the sample fluid can be measured by optical and electronic methods with relatively high accuracy.

The exemplary embodiments allow a measurement of the sample transparency as a function of sample thickness in a single experiment. These measurements permit a determination of the particle size parameters in the sample fluid using an integral scattering approach, such as that as disclosed in the Schnablegger et al document. At the same time the parameters of the largest particles can be determined using a single-particle approach. The combination of these two different approaches (that is, integral and differential) permits an improvement in the accuracy and reliability of the measurements.

In exemplary embodiments, laser light extinction and multiple light scattering by the particles are negligible for a "sheet" of a typical slurry. At the same time the slurry flow requires no dilution and therefore the size distribution of the particles in the slurry will not be distorted.

Figure 6:
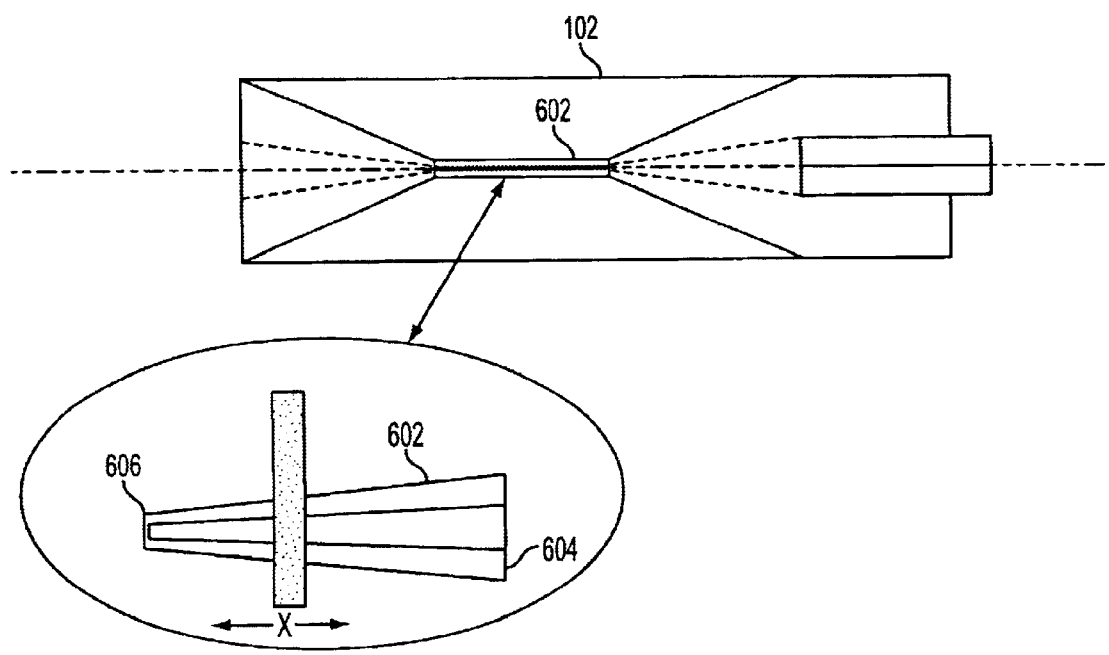
FIG. 6 shows an optical cuvette according to a fifth exemplary embodiment of the present invention.

In a fifth exemplary embodiment shown in FIG. 6, the "flat" part 602 of the optical cuvette actually resembles a converging wedge, with an angle typically in the range of 0.5–5 degrees, or any other desired angle. The flow channel defining the flat part of the cuvette is no longer defined by two parallel surfaces; instead, it is a wedge-shaped channel, having a spacing that changes gradually from one edge of the sample flow to the other. The position of the irradiating light beam can be changed along the X-axis to choose the desired sample flow thickness.

In the FIG. 6 embodiment, the width of the flow channel changes from a maximum value at the sample/sheath flow inlet (e.g. 1 mm) to a minimum value at the sample/sheath flow outlet (e.g. 0.1 mm). The gradual change in the flow channel thickness causes a variation in the focused sample fluid thickness from a maximum value at the inlet to a minimum value at the outlet. The sample transparency will vary accordingly.

The sample fluid flow is illuminated as described above, and the scattered and/or transmitted light intensity signal is measured at a certain distance from the inlet, 604. In the absence of significant sample transparency, and/or the presence of excessive multiple light scattering, the measuring position along the X-axis can be adjusted. If the focused sample fluid is not transparent enough, the measuring point is shifted toward the cuvette outlet 606, where the focused sample fluid is thinner. If the optical thickness of the sample fluid is too small (for example, <0.5, or any other desired threshold), the measuring point can be shifted towards the cuvette inlet 604, thereby increasing the sensing volume and improving the large-particle statistics and the accuracy of the measurement.

Figure 7:
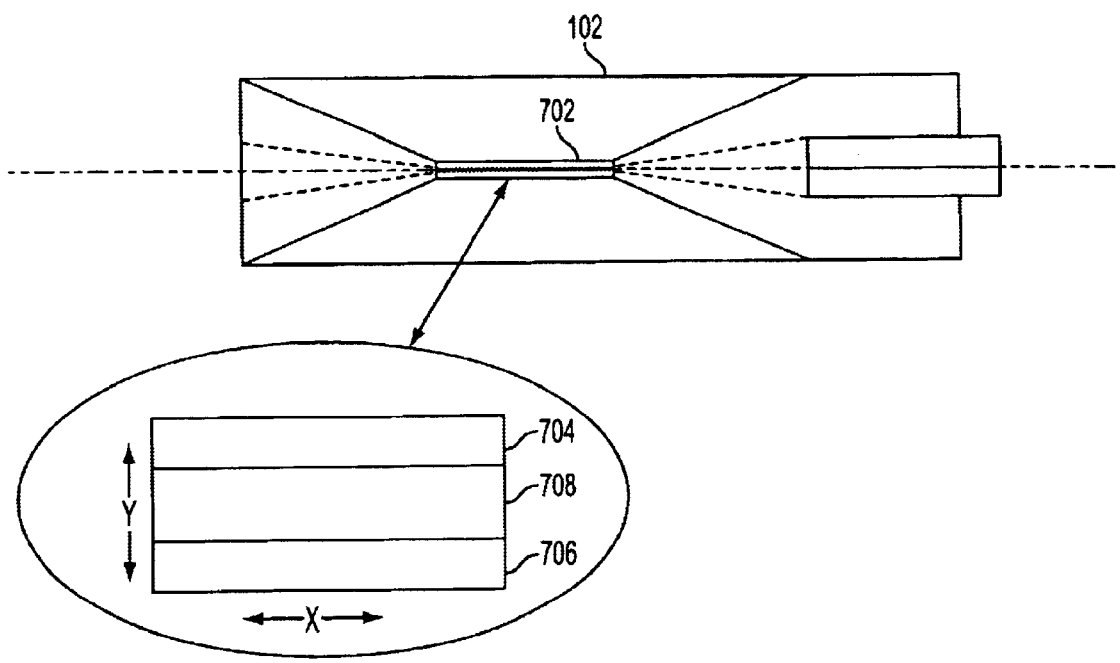
FIG. 7 shows an optical cuvette according to a sixth exemplary embodiment of the present invention.

In a sixth exemplary embodiment of the present invention as shown in FIG. 7, the thickness of the flow channel in the flat part 702 of the cuvette can be adjusted to control the sample fluid thickness and, accordingly, the sample transparency. The width of the flow channel defining the flat part of the cuvette can be changed depending on the desired final focused sample flow thickness. To achieve a variation in the channel thickness, the cuvette is configured using two symmetrical optical parts 704 and 706, such as Dove prisms, separated by an elastic spacer 708 formed of, for example, O-ring cord (for example, 65–75 Durometer Black Buna-N from McMaster-Carr Inc.) or any elastic material, as illustrated in FIG. 9. External controlled pressure can be applied on these two opposing parts using screws, hydraulic or pneumatic actuators, electromagnetic actuators or any other means of controlled displacement to cause a shrinkage in the spacer to a level which depends on the applied pressure and Young's modulus of elasticity for the spacer. This will allow control of the sample transparency, because the focused fluid sample thickness can have a known relationship (e.g., be proportional) to the flow channel thickness. In the FIG. 7 embodiment, the optical signal from the particles can be measured anywhere in the flat part of the cuvette. This allows an increase in the efficient sensing volume by extension in the X and Y directions (along and across of the compressed flow), while keeping the focused sample fluid thickness at a predetermined optimal level.

Figure 8A:
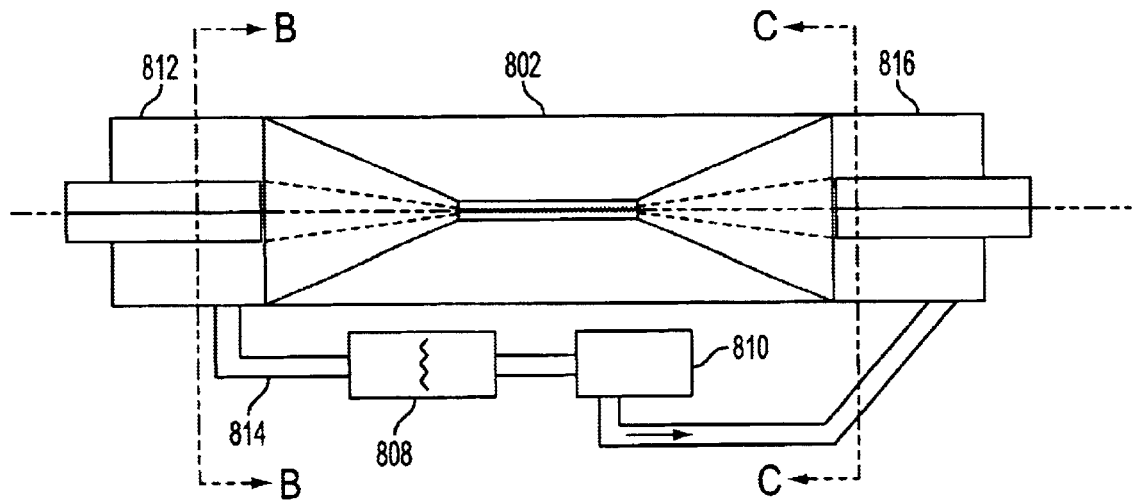
FIGS. 8A–8C show an optical cuvette/sensor having a symmetrical concentrated sample fluid inlet and outlet.
Figure 8B:
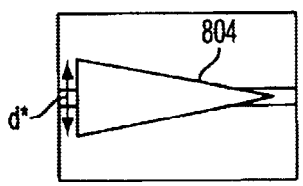
Figure 8C:
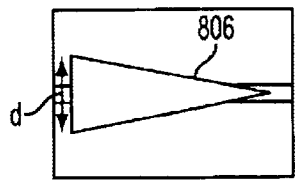

In FIGS. 8A–8C, an exemplary optical cuvette/sensor 802 having a symmetrical concentrated sample fluid inlet and outlet is illustrated, wherein the latter outlet is used to capture the original concentrated sample fluid and return the major part of it to the production line from which it was originally extracted. The width of the slit in the outlet part 804 of the cuvette shown in FIG. 8B, hereinafter referred to as d*, is equal to or less than the width of the slit used to introduce the concentrated sample in the inlet part 806 shown in FIG. 8C, hereinafter referred to as d. Those skilled in the art will appreciate that any of the slit configurations described herein, as well as variations of the slit configurations as modified in any desired fashion to achieve a reduction in the cross section of the sample, can be used in the FIG. 8A embodiment.

In FIG. 8A, a filtering means is represented as including a filter 808, which can be any desired fluid filter for removing at least undesired particulate and/or contaminants from the fluid. An associated pump 810 is provided as a pumping means, and can be any device for transporting fluid. Fluid at a fluid outlet 812 located downstream of the hydrodynamic focusing is collected in a conduit 814, and pumped through filter 808 back to a fluid inlet 816 for use in ongoing hydrodynamic focusing.

Figure 9A:
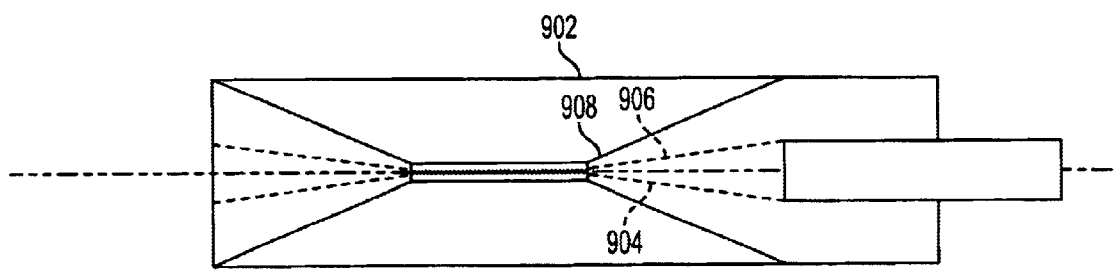
FIGS. 9A and 9B show an exemplary set-up to monitor and control velocity matching of concentrated sample fluid and sheath fluid flow rates into a cuvette.

FIG. 9 illustrates an exemplary method to control the velocity match of sample and sheath flows supplied to the cuvette. In FIG. 9, the optical cuvette is labeled 902. Referring to FIG. 9A, a laser beam 904 supplied from a light source, is directed to the inlet of the flat part of the cuvette 902. A reflected beam 906 is detected to measure the sheath flow transparency before entering the inlet 908.

Figure 9B:
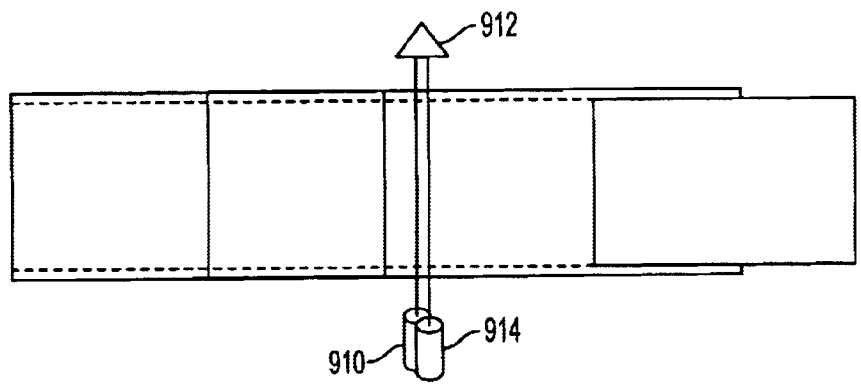

FIG. 9B shows a side view of the configuration illustrated from a top view in FIG. 9A. Referring to FIG. 9B, a light source 910 is illustrated as supplying light in the direction of beam deflector 912 which reflects light toward the light detector 914. The light detector provides a measure of the sheath flow transparency. In the case of a velocity mismatch, turbulence mixing of the sample and sheath flows can occur and the sheath flow transparency can vary from a predetermined threshold which can, for example, be determined empirically. A comparison of the output from the light detector with the threshold can be achieved using any technique, including the use of a computer processor. In another embodiment the light detector 914 is placed in a position opposite beam deflector 912. In this case, the turbidity can be measured on one side of the focused slurry flow. One side measurement can be sufficient to conclude the existence of a velocity mismatch because turbulent spreading of the center flow with particles will typically occur in both directions.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

I claim:

1. Method for detecting individual particles in a flowable sample, comprising the steps of:
    hydrodynamically focusing the sample, the sample being opaque to at least a first range of wavelengths of lightwaves;
    measuring transparency of the sample;
    compressing the sample to create a compressed sample which is transparent to at least one of the wavelengths of lightwaves; and
    identifying characteristics of individual particles contained in the compressed sample.

2. Method according to claim 1, wherein the step of hydrodynamically focusing compressing includes:
    elongating the sample in a first dimension.

3. Method according to claim 2, wherein the step of compressing comprising:
    compressing the sample in a second dimension which is different from the first dimension.

4. Method according to claim 1, wherein the step of hydrodynamically focusing includes:
    surrounding the sample with a clear liquid.

5. Method according to claim 1, wherein the step of compressing includes:
    compressing the sample using two Dove prisms.

6. Method according to claim 1, wherein the step of hydrodynamically focusing includes:
    increasing the sensing volume to a value selected as a function of light scattering which occurs for the at least one wavelength.

7. Method according to claim 1, wherein the step of compressing includes:
    substantially eliminating multiple scattering of lightwaves for the at least one wavelength.

8. Method according to claim 1, wherein the step of compressing is performed with a compression ratio of at least 100.

9. Method according to claim 1, wherein the step of identifying includes:
    optically examining a sample using a lightwave of the at least one wavelength to irradiate the sample.

10. Method according to claim 1, wherein the step of identifying includes:
    optically examining the sample using a pulsed light source.

11. Method according to claim 1, wherein the step of identifying includes:
    detecting particles having diameters on the order of 0.5 micrometers to 5 micrometers.

12. Method according to claim 1, wherein the step of identifying includes:
    detecting particles having diameters on the order of 5 micrometers to 10 micrometers.

13. Method according to claim 1, wherein the characteristics include at least one of detecting the size of individual particles contained in the sample and the concentration of the sample.

14. Method according to claim 1, wherein the step of identifying includes:
    directly detecting the characteristics of individual particles by sensing lightwaves transmitted through the sample.

15. Method according to claim 14, wherein the step of detecting is performed using a CCD camera to detect characteristics of the individual particles in response to optical signals received from the slurry.

16. Method according to claim 14, wherein the step of detecting is performed using a photodiode camera to detect characteristics of the individual particles in response to optical signals received from the slurry.

17. Method according to claim 1, wherein the sample is a slurry.

18. Method according to claim 1, comprising:
    diluting the sample prior to the step of compressing.

19. Method according to claim 1, comprising the step of:
    discontinuing flow of the sample in response to determining a predetermined characteristic of the sample.

20. Method according to claim 19, wherein the predetermined characteristic is a concentration of particles in excess of a predetermined size.

21. Method according to claim 19, wherein the predetermined characteristic is a concentration of particles of a given size exceeding a predetermined value.

22. Apparatus for detecting individual particles in a flowable sample, comprising:

means for hydrodynamically focusing the sample, the sample being opaque to at least a first range of wavelengths of lightwaves;

means for compressing the sample to create a compressed sample which is transparent to at least one of the wavelengths of lightwaves; and means for identifying characteristics of individual particles contained in the compressed sample.

23. Apparatus according to claim 22, wherein the compressing means includes:

a slit for supplying the sample, a position of the slit being selected as a function of a concentration of the individual particles in the sample.

24. Apparatus according to claim 22, wherein the compressing means includes:

a slit for receiving the sample, wherein a width of the slit is selected as a function of a concentration of the individual particle in the sample.

25. Apparatus according to claim 23, comprising:

coaxial tubes for varying the width of the slit.

26. Apparatus according to claim 22, wherein the hydrodynamically focusing means includes:

means for surrounding the sample by clear liquid.

27. Apparatus according to claim 22, wherein the hydrodynamically focusing means includes:

a slit for supplying the sample; and an additional slit for receiving a clean liquid, a ratio of a width of the additional slit to the slit for supplying the sample being at least 10:1.

28. Apparatus according to claim 27, wherein the clean liquid and the sample are matched in pH.

29. Apparatus according to claim 27, wherein the clean liquid is water.

30. Apparatus according to claim 27, comprising:

means for filtering and recirculating the clean liquid.

31. Apparatus according to claim 22, wherein the compressing means comprises:

at least two Dove prisms for compressing the sample in at least one dimension to render the sample transparent to lightwaves of a predetermined wavelength.

32. Apparatus according to claim 22, wherein the identifying means includes:

an optical detector to detect an optical signal.

33. Apparatus according to claim 32, wherein the optical signal is transmitted through the sample.

34. Apparatus according to claim 32, wherein the optical signal is reflected from the sample.

35. Apparatus according to claim 32, wherein the optical detector is a CCD camera.

36. Apparatus according to claim 28, wherein the optical detector is a photodiode.

* * * * *